United States Patent [19]

Landesberg

[11] Patent Number: 5,201,025

[45] Date of Patent: Apr. 6, 1993

[54] DUAL PURPOSE ELECTRIC VAPORIZER FOR TABLETS

[75] Inventor: Bruno Landesberg, Tel Aviv, Israel

[73] Assignee: Sano - Bruno's Enterprises Ltd., Hod Hasharon, Israel

[21] Appl. No.: 781,805

[22] Filed: Oct. 28, 1991

[51] Int. Cl.[5] .................................... A61M 16/00
[52] U.S. Cl. ..................... 392/392; 392/390
[58] Field of Search ................... 392/390, 391, 392

[56]  References Cited
U.S. PATENT DOCUMENTS

| | | | |
|---|---|---|---|
| 2,513,919 | 7/1950 | Costello | 392/390 |
| 2,691,716 | 10/1954 | Wellens | 392/390 |
| 2,942,090 | 6/1960 | Diehl | 392/390 |
| 3,895,928 | 7/1975 | Moran | 392/390 |
| 4,467,177 | 8/1984 | Zobele | 392/390 |

OTHER PUBLICATIONS

Abstract, 2552-902 of W. Ger. patent document Nov. 14, 1985.
Abstract, 3701-499 of W. Ger. patent document Jul. 28, 1988.
Abstract, 3510-641 of W. Ger. patent document Sep. 25, 1986.

Primary Examiner—Teresa J. Walberg
Attorney, Agent, or Firm—Browdy and Neimark

[57] ABSTRACT

A dual purpose electric vaporizer comprising a container having an electric heating element heated by an electric current, and the heating element connected to an external electric power source. The container has a double deck tablet containing means, for the tablets to be vaporized. The first of the deck containing means is placed at a position close to the heating element, and another deck is positioned at an elevated position above the first deck, at a substantial distance from the heating element. The first containing means can thus be loaded with an insecticide repellant tablet in the lower deck, having a higher evaporating temperature, and the upper deck can be loaded with an air freshener tablet evaporating at a lower temperature.

5 Claims, 1 Drawing Sheet

DUAL PURPOSE ELECTRIC VAPORIZER FOR TABLETS

This invention relates to a dual purpose electric vaporizer for tablets containing either insect repeller, or air freshener in any required combination.

BACKGROUND OF THE INVENTION

Several types of electric vaporizers are known in the prior art for vaporizing insect repellers from tablets. These vaporizers usually operate at temperatures of 120° C. (measured at the contact area of the tablet and healing element). Such temperature was found to be too high for use for vaporizing air freshener tablets, which at such temperature may either decompose, or vaporize instantaneously thus loosing the long term slow release effect. Such as the system described in EP 104758 (by Spector D).

Several vaporizers were tried in the prior art to overcome this draw back. The best known is a Japanese version, which introduced the tablet contact area at a position distanced from the heating element, the tablet contact plate was placed at a position below the heating element and thus the vaporized air freshener vapor was released at a lower rate.

The major disadvantages of this system is the fact that only one tablet can be used at the time. The other disadvantage is that the vaporized air freshener rises through the device whereby some of the vapor may come into contact with the heating element at a temperature much above the desired one, resulting possible decomposition of the vapor; and other parts of the vapor may condense on the cooler parts of the device.

Another system describes a double tablet canister placed on both sides of a heating element as described in DE3701499 by Global-Werk. This device has a disadvantage of having both tablets exposed to the high temperature of the heating element.

SUMMARY OF THE INVENTION

It is the purpose of the invention to provide a dual purpose electric vaporizing device for use with tablets, having double decker slots for tablet positioning facility one on top of each other to enable use of two tablets, one at a close position to the heating element, suitable for tablets to be vaporized at lower temperatures.

The advantages of this design can be summarized as follows:

a) One could use the bottom deck for vaporizing regular insecticide repeller, and the top deck for vaporizing air freshener tablets.
b) One could use both decks (upper and lower) for vaporizing an insecticide repeller, thus prolonging the effective period of the tablets.
c) One could use the upper deck only for vaporizing an air freshener.
d) One could use the bottom deck only for vaporizing an insecticide repeller.

The dual purpose electric vaporizer herein provided comprises a container having an electric heating element heated by an electric current and said heating element is connectable to an external electric power source; and said container having a double deck containing means for tablets to be vaporized; and one of said tablets containing means is placed at a position closed to said heating element, and the other tablet containing means is positioned at an elevated position above the first containing means at a distance away from said heating element; so that when said tablet containing means is loaded with either one or two tablets containing an insecticide repellant, an air freshener or the like; and said heating element is connected to an external electric power source, said tablet placed in said upper deck container means shall be exposed to a lower temperature than the tablet placed in said lower container means.

In the preferred embodiment the dual electric vaporizer described above has contains means in form of double decker open slots into which said tablets can be introduced.

In the preferred embodiment said container and tablet containing means are made of plastic.

In the preferred embodiment said upper deck containing means is used in particularly for air freshener vapourisable tablets, and lower deck for an insecticide repeller tablet.

In another preferred embodiment both decks are used for insecticide repeller tablets, thus resulting a prolonged effect of the insecticide repeller.

The invention can be best described with reference to the attached illustrations:

DETAILED DESCRIPTION OF THE INVENTION

Figure 1:
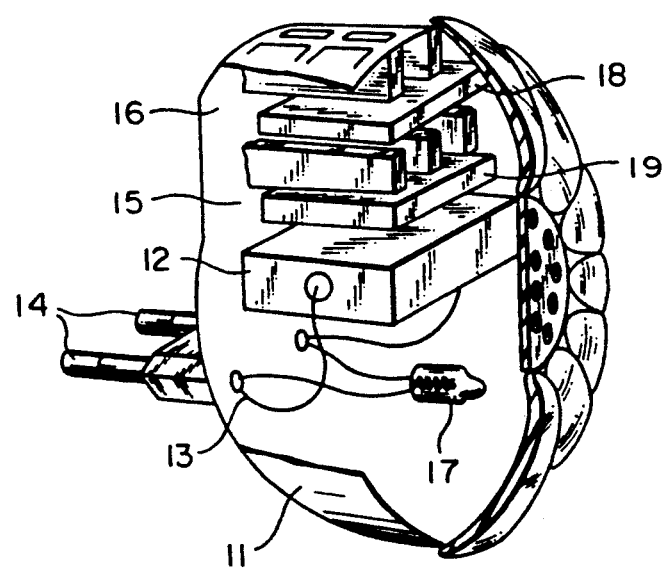
FIG. 1 illustrates a cross sectional three dimensional drawing of the dual deck vaporizer.

The vaporizer described in FIG. 1 comprises a plastic container 11, having in it a heating plate 12, connected to an electric wire 13 connected to the electric mains by the plug pins 14.

The lower tablet containing slot like means 15 in a position close to the plate 12, and the upper tablet slot like containing means 16 distanced from the plate 12.

A small electric bulb 17 is switched on when the device is in operation.

The upper containing means 16 is usually loaded with an air freshener vapourisable tablet 18 and the lower deck 15 is loaded with an insecticide repelling tablet 19.

Alternatively one could use both decks 15, 16 for the insecticide repeller placing in both the same tablets 19; or one could use the device for either one purpose by placing only an air freshener tablet 18 into the upper deck 16; or only an insecticide repeller tablet 19 into the deck 15.

The invention has been described in reference to the attached drawings but it should be appreciated that other combinations are also possible whereby the distanced tablet containing means is placed at other positions away from the heating element. They should all be considered as part of this invention.

What is claimed:

1. A dual purpose electric vaporizer comprising a container having an electric heating element heated by an electric current and said heating element is connectable to an external electric power source; and said container having a double deck containing means for tablets to be vaporized located above said heating element; and one lower deck of said containing means for tablets is placed at a position close to said heating element, and the upper deck of said containing means for tablets is positioned at an elevated position above the containing means close to said heating element, at a distance away from said heating element; so that when said containing means for tablets is loaded with either one or two tablets containing either an insecticide, repellant, or an air freshener; and said heating element is connected to an external electric power source, said tablet placed in said upper deck of said container means shall be exposed to a lower temperature than the tablet placed in said lower deck of said container means.

2. A dual electric vaporizer as in claim 1 wherein said containing means are in form of double decker open slots into which said tablets can be introduced.

3. A dual electric vaporizer as in claim 1 wherein said container and slots are produced of plastic.

4. A dual electric vaporizer as in claim 1 wherein said upper deck containing means is loaded with a tablet of an air refreshener and said lower deck containing means is loaded with an insecticide repeller.

5. A dual electric vaporizer as in claim 1 wherein both of said containing means are loaded with an insecticide repeller thus resulting in a prolonged effect of said repeller.

* * * * *